(12) United States Patent
Pinel et al.

(10) Patent No.: US 8,097,590 B2
(45) Date of Patent: Jan. 17, 2012

(54) α-MSH-ANTAGONIST DIPEPTIDE CONJUGATES

(75) Inventors: Anne-Marie Pinel, Toulouse (FR); Pascal Verdie, Saint Mathieu de Treviers (FR); Pascaline Dubs, Montpellier (FR); Jean Martinez, Caux (FR); Gilles Subra, Juvignac (FR)

(73) Assignees: Centre National de la Recherche Scientifique (CNRS), Paris (FR); Institut Europeen de Biologie Cellulaire, Ramonville St. Agne (FR); Universite de Montpellier I, Montpellier (FR); Universite de Montpellier II, Montpellier (FR)

( * ) Notice: Subject to any disclaimer, the term of this patent is extended or adjusted under 35 U.S.C. 154(b) by 1143 days.

(21) Appl. No.: 11/596,286

(22) PCT Filed: May 10, 2005

(86) PCT No.: PCT/FR2005/001164

§ 371 (c)(1),
(2), (4) Date: May 23, 2007

(87) PCT Pub. No.: WO2005/115174

PCT Pub. Date: Dec. 8, 2005

(65) Prior Publication Data

US 2007/0231284 A1    Oct. 4, 2007

(30) Foreign Application Priority Data

May 11, 2004 (FR) .................................... 04 05069
Oct. 22, 2004 (FR) .................................... 04 11279

(51) Int. Cl.
C07C 229/00    (2006.01)

(52) U.S. Cl. .............................. 514/19; 514/558; 424/62
(58) Field of Classification Search .......................... None
See application file for complete search history.

(56) References Cited

U.S. PATENT DOCUMENTS

| | | | |
|---|---|---|---|
| 5,674,839 A | 10/1997 | Hruby et al. | |
| 5,714,576 A | 2/1998 | Hruby et al. | |
| 5,719,126 A | 2/1998 | Nordlund et al. | |
| 5,786,332 A | 7/1998 | Girten et al. | |
| 5,830,994 A | 11/1998 | D'Hinterland et al. | |
| 6,054,556 A | 4/2000 | Hruby et al. | |
| 6,228,840 B1 | 5/2001 | Wei et al. | |
| 6,245,342 B1 | 6/2001 | Golz-Berner et al. | |
| 6,337,315 B1 | 1/2002 | Mahe et al. | |
| 6,372,717 B1 | 4/2002 | Greff | |
| 6,579,848 B1 | 6/2003 | Hearing, Jr. | |
| 2003/0194445 A1 | 10/2003 | Kuhner et al. | |
| 2004/0010010 A1 | 1/2004 | Ebetino et al. | |
| 2005/0187164 A1 | 8/2005 | Pinel | |

FOREIGN PATENT DOCUMENTS

| | | |
|---|---|---|
| EP | 0 389 950 A1 | 10/1990 |
| EP | 0 669 938 B1 | 9/1995 |
| EP | 0 949 902 B1 | 10/1999 |
| EP | 0 972 522 B1 | 1/2000 |
| EP | 1 174 437 A1 | 1/2002 |
| FR | 1327363 | 5/1962 |
| FR | 2805744 A1 | 9/2001 |
| FR | 2 810 323 A1 | 12/2001 |
| GB | 1 000 897 | 8/1965 |
| WO | WO 95/08564 A1 | 3/1995 |
| WO | WO 98/07744 A1 | 2/1998 |
| WO | WO 98/25584 A1 | 6/1998 |
| WO | WO 01/64178 A1 | 9/2001 |
| WO | WO 01/98362 A2 | 12/2001 |
| WO | WO 02/085925 A2 | 10/2002 |
| WO | WO 03/064458 A2 | 8/2003 |
| WO | WO 03/095474 A2 | 11/2003 |
| WO | WO 2004/099237 A1 | 11/2004 |
| WO | WO 2004/110341 A2 | 12/2004 |
| WO | WO 2005/116068 A1 | 12/2005 |

OTHER PUBLICATIONS

Stverteczky et al., Acta Chimica Academiae Scientiarum Hungaricae, 1975, vol. 87, No. 3, pp. 269-283.*
Baumann et al., "Specificity of α-chyrnotrypsin dipeptide substrates," FEBS Letters, Jun. 1970, 8(5), 257-260.
Beekman et al., "Synthetic peptide vaccines: palmitoylation of peptide antigens by a thioester bond increases immunogenicityk," J. Peptide Res., 1997, 50: 357-364.
Chhajlani, Vijay, "Characterization of a Putative α-MSH Antagonist 153N-6 at Melanocortin Receptor Subtypes by Radioligand Binding," Peptides, 1996, 17(2), 349-351.
Cone et al., "The Melanocortin Receptors: Agonists, Antagonists, and the Hormonal Control of Pigmentation," Recent Progress in Hormone Research, 1996, 51:287-317.
Feliu et al., "Spiroimidazolidinone Library Derivatives on SynPhase Lanterns," J. Comb. Chem., 2003, 4:356-361.

(Continued)

*Primary Examiner* — Christopher R. Tate
*Assistant Examiner* — Roy Teller
(74) *Attorney, Agent, or Firm* — Foley & Lardner LLP

(57) ABSTRACT

The invention relates to a dipeptide conjugate having general formula I, AA2-AA1-NH$_2$, wherein A represent the radical corresponding to a monocarboxylic acid with general formula II, HOOC—R, in which: R represents a linear or branched aliphatic radical at $C_1$-$C_{24}$, which is optionally substituted by a hydroxyl group and which can comprise one or more unsaturations, preferably between 1 and 6 unsaturations, and/or which can comprise a phenyl group or lipoic acid or the reduced form thereof, dihydrolipoic acid or N-lipoyllysine; and AA1 and AA2 represent identical or different amino acids which are selected from the group containing Ala, Asn, Cys, Gln, Gly, Ile, Leu, Met, Phe, Pro, Ser, Thr, Trp, Tyr, Val, Asp, Glu, Arg, His, Lys, Orn, Dap, Dab, the corresponding homo-amino acids and the corresponding beta-amino acids in the form of enantiomers or diastereoisomers and mixtures thereof, including racemic mixtures.

9 Claims, No Drawings

OTHER PUBLICATIONS

Haskell-Luevano et al., "Truncation Studies of α-Melanotropin Peptied Identify Tripeptide Analogues Exhibiting Prolonged Agonist Bioactivity," Peptides, 1996, 17(6), 995-1002.

Holder et al., "Characterization of aliphatic, cyclic, and aromatic N-terminally 'capped' His-D-Phe-Arg-Trp-NH$_2$ tetrapeptides at the melanocortin receptors," European Journal of Pharmacology, 2003, 462:41-52.

Holder et al., "Structure-Activity Relationships of the Melanocortin Tetrapeptide Ac-His-D-Phe-Arg-Trp-NH$_2$ at the Mouse Melanocortin Receptors. 4. Modifications at the Trp Position," J. Med. Chem., 2002, 45:5736-5744.

Holder et al., "Structure-Activity Relationships of the Melanocortin Tetrapeptide Ac-His-D-Phe-Arg-Trp-NH2 at the Mouse Melanocortic Receptors. 1. Modifications at the His Position," J. Med. Chem., 2002, 45:2801-2810.

Hruby et al., "Design, Synthesis, and Conformation of Superpotent and Prolonged Acting Melanotropins," Ann. N.Y. Acad. Sci., 1993, 680:51-63.

Jacubovich et al., "Tumour-associated Antigens in Culture Medium of Malignant Melanoma Cell Strains," Cancer Immunol. Immunother., 1979, 7:59-64.

Jayawickreme et al., "Discovery and Structure-Function Analysis of α-Melanocyte-stimulating Hormone Antagonists," J. Biol. Chem., Nov. 25, 1994, 269(47), 29846-29854.

Lerner et al., "Effect of α- and β-melanocyte stimulating hormones on the skin colour of man," Nature, Jan. 21, 1961, 189:176-179.

Lopez-Fandino et al., "Protease-Catalyzed Synthesis of Oligopeptides in Heterogenous Substrate Mixtures," Biotechnology and Bioengineering, 1994, 43:1024-1030.

Lu et al., "Agouti protein is an antagonist of the melanocyte-stimulating-hormone receptor," Nature, Oct. 27, 1994, 371:799-802.

Mountjoy et al., "The Cloning of a Family of Genes That Encode the Melanocortin Receptors," Science, Aug. 28, 1992, 257:1248-1251.

Nijenhuis et al., "Discovery and in vivo evaluation of new melanocortin-4 receptor-selective peptides," Peptides, 2003, 24:271-280.

Ollmann et al., "Antagonism of Central Melanocortin Receptors in Vitro and in Vivo by Agouti-Related Protein," Science, Oct. 3, 1997, 278:135-138.

Quillan et al., "Combinatorial diffusion assay used to identify topically active melanocyte-stimulating hormone receptor antagonists," Proc. Natl. Acad. Sci. USA, Mar. 1995, 92:2894-2898.

Shutter et al., "Hypothalamic expression of ART, a novel gene related to agouti, is up-regulated in obese and diabetic mutant mice," Genes & Development, 1997, 11:593-602.

Stverteczky et al., "Synthesis of N-acyl-oligopeptides of potential antitubeculotic activity," Acta Chim. Acad. Sci. Hungaricae, Tomus, 1975, 87(3), 269-283.

Takahama, Motohide, "α-MSH discovered in primary root of sesame seeds, and trial on remelanization of gray hairs by their extract: immunohistochemical study," Journal of Dermatological Science, Apr. 2004, (34(2), p. 148, XP002302532 & 19$^{th}$ Annual meeting of the Japanese Society for Investigative Dermatology. Kyoto, Japan, Apr. 14-16, 2004, one page.

Vogler et al., "Basic peptides containing fatty acids with an antibacterial action," 1964, 47:526-544, ZP002062066, and its English translation.

Office Action issued by the Examiner in U.S. Appl. No. 11/596,041 on Mar. 15, 2010.

U.S. Appl. No. 11/596,041, filed Jun. 28, 2007, Martinez et al.

Office Action issued by the Examiner in U.S. Appl. No. 11/596,041 on Sep. 29, 2009.

Al-Obeidi et al., "Synthesis and Biological Activities of Fatty Acid Conjugates of a Cyclic Lactam α-Melanotropin," J. Med. Chem., 1992, 34:118-123.

Hadley et al., "Biological Activities of Melanotropic Peptide Fatty Acid Conjugates," Pigment Cell Research, 1991, 4:180-185.

Haskell-Luevano et al., "Characterization of Melanocortin NDP-MSH Agonist Peptide Fragments at the Mouse Central and Peripheral Melanocortin Receptors," J. Med. Chem., 2001, 44, 2247-2252.

Haskell-Luevano et al., "Discovery of Prototype Peptidomimetic Agonists at the Human Melanocortin Receptors MC1R and MC4R," J. Med. Chem., 1997, 40:2133-2139.

Hiltz et al., "Alpha-MSH Peptides Inhibit Acute Inflammation and contact Sensitivity," Peptides, 1990, 11:979-982.

Koikov et al., "Analogs of sub-nanomolar hMC1R agonist LK-184 [Ph(CH2)3CO-His-D-Phe-Arg-Trp-NH2]. An additional binding site within the human melanocortin receptor 1?", Bioorganic & Medicinal Chemistry Letters, 2004, 14:3997-4000.

Koikov et al., "Sub-Nanomolar hMC1R Agonists by End-Capping of the Melanocortin Tetrapeptide His-D-Phe-Arg-Trp-NH2," Bioorganic & Medicinal Chemistry Letters, 2003, 13:2647-2650.

Lipton, James M., "Modulation of Host Defense by the Neuropeptide α-MSH," Yale Journal of Biology and Medicine, 1990, 63:173-182.

Tatro et al., "Specific Receptors for α-Melanocyte-Stimulating Hormone Are Widely Distributed in Tissues of Rodents," Endocrinology, 1987, 121(5): 1900-1907.

Todorovic et al., "N-Terminal Fatty Acylated His-DPhe-Arg-Trp-NH2 Tetrapeptides: Influence of Fatty Acid Chain Length of Potency and Selectivity at the Mouse Melanocortin Receptors and Human Melanocytes," J. Med. Chem., 2005, 48:3328-3336.

Yasumura et al., "Establishment of Four Functional, Clonal Strains of Animal Cells in Culture," Science, 1996, 154:1186-1189.

International Search Report issued in application No. PCT/FR2005/001166 on Oct. 10, 2005.

International Search Report issued in application No. PCT/FR2005/001165 on Apr. 21, 2006.

French Search Report issued in application No. FR 655954 on May 11, 2005.

French Search Report issued in application No. FR 1056469 on Jan. 5, 2011.

Campos et al., "The Conformational Versatility of DNA in the Presence of Basic Peptides," Studia Biophysica, vol. 81, No. 1, pp. 3-14, May 1980.

Notice of Allowance issued in U.S. Appl. No. 11/596,041 by the Examiner on Dec. 17, 2010.

* cited by examiner

α-MSH-ANTAGONIST DIPEPTIDE CONJUGATES

This application is a National Stage application of PCT/FR2005/001164, filed May 10, 2005, which claims priority from French patent applications FR 0405069, filed May 11, 2004, and 0411279, filed Oct. 22, 2004. The entire contents of each of the aforementioned applications are incorporated herein by reference.

This invention relates to new alpha-MSH antagonist dipeptide conjugates and their use as a medicine or as a depigmenting agent.

Melanocortine receptors belong to the superfamily of seven transmembrane receptors coupled to protein G and they stimulate the AMPc signal transduction channel (Cone et al. *Recent Prog. Horm. Res.* 1996, 51, pages 287-317). The melanocortine system is involved in many physiological channels including pigmentation, inflammation, the erectile function, food behavior, energy homeostasis, weight homeostasis and the exocrine glands function. The endogenic agonist ligands for these melanocortine receptors are derived by post-translational modification of the transcript of the proopiomelanocortine gene, that during differential treatment causes generation of α, β and γ hormones stimulating melanocytes (MSH) and corticotrophine (ACTH). Subtypes of melanocortine receptors are activated by all endogenic melanocortine peptides, except for the melanocortine $MC_2$ receptor that is only stimulated by corticotrophine. The family of melanocortine receptors also has two endogenic antagonists, namely agouti and protein related to agouti (AGRP) (Lu et al. *Nature* 1994, 371, pages 799-802, Ollmann et al., *Science* 1997, pages 135-138, Shulter et al., *Genes Dev.* 1997, 11, pages 593-602) that are the only known antagonists discovered at the moment existing in the natural state of these receptors coupled with protein G. These are polypeptides of 132 and 49 amino acid residues respectively. The most studied melanocortine receptor ligands are MC, receptor ligands of melanocortine of the skin that are involved in pigmentation and coloring of animal hair coat (Hruby et al. *Ann. N.Y. Acad. Sci.* 1993, 680, pages 51-63; Lerner et al. *Nature* 1961, pages 189, 176; Mountjoy et al. *Science* 1992, 257, pages 1248-1251).

Nonapepdide 153 N-6 (Jayawickreme et al., *J. Biol. Chem.* 1994, 269, pages 29846-29854) (H-Met-Pro-D-Phe-Arg-d-Trp-Phe-Lys-Pro-Val-$NH_2$: Ki=11 nM) is a synthetic antagonist of the receptor $MC_1$. However, this compound has a high molecular weight and therefore a very limited therapeutic or cosmetic activity. Its size makes it difficult to optimize and its bioavailability is limited. It is also expensive and difficult to prepare.

Tripeptide D-Trp-Arg-Leu-$NH_2$ (Proc. Natl. Acad. Sci. (1995), 92, pages 2894-2898) also has an antagonist activity. However, it contains tryptophan that is an unstable amino acid and therefore can cause stability problems during storage.

Patent EP 1 174 437 describes di- or tripeptides comprising a naphthyl group and in particular a naphthylalanyl group. However, the presence of the naphthyl group increases the fabrication price of the product. Furthermore in some countries such as Japan, unnatural amino acid based peptides cannot be sold for cosmetic applications. Furthermore, no dipeptide activity is indicated.

Surprisingly, the inventors discovered that dipeptides conjugated at the C-terminal with carboxylic acids have an antagonist activity of the MSH alpha. These antagonists have a very low molecular weight and are therefore easy to optimize, they have good bioavailability and are very easy to prepare.

Therefore, this invention relates to a dipeptide conjugate with general formula I below:

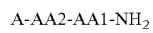

$$A\text{-}AA2\text{-}AA1\text{-}NH_2 \qquad \qquad I$$

in which
A represents the radical corresponding to a monocarboxylic acid with the following general formula II:

$$HOOC\text{—}R \qquad \qquad II$$

in which R represents
a linear or branched aliphatic radical in $C_1$-$C_{24}$, optionally substituted by a hydroxyl group, which can comprise one or more unsaturations, preferably between 1 and 6 unsaturations, and/or which can comprise a phenyl group,
or lipoic acid or the reduced form thereof, dihydrolipoic acid or N-lipoyllysine.

AA1 and AA2 represent identical or different amino acids chosen from the group consisting of Ala, Asn, Cys, Gln, Gly, Ile, Leu, Met, Phe, Pro, Ser, Thr, Trp, Tyr, Val, Asp, Glu, Arg, His, Lys, Orn, Dap, Dab, the corresponding homo-amino acids and the corresponding beta-amino acids,
in the form of enantiomers or diastereoisomers and mixtures thereof including racemic mixtures.

Amino acids in the dipeptide conjugate with formula (I) may have a D, L or DL configuration if it is not specified otherwise.

Thus, dipeptide conjugates with formula (I) may comprise one or more asymmetric carbon atoms. Therefore, they may exist in the form of enantiomers or diastereoisomers. The invention includes these enantiomers, diastereoisomers and mixtures thereof, including racemic mixtures.

Within the framework of this invention, the following abbreviations have the following meanings:
Ala, Alanine,
Asn, Asparagine,
Cys, Cystein,
Gln, Glutamine,
Gly, Glycine,
Ile, Isoleucine,
Leu, Leucine,
Met, Methionine,
Phe, Phenylalanine or similar, particularly a halogenated derivative, and particularly para-fluoro-Phe, Homo-Phe, para-nitro-Phe or phenylglycine
Pro, Proline,
Ser, Serine,
Thr, Threonine,
Trp, Tryptophan,
Tyr, Tyrosine,
Val, Valine,
Asp, Aspartic acid,
Glu, Glutamic acid,
Arg, Arginine,
His, Histidine,
Lys, Lysine,
Orn, Ornithine,
Dap, Diaminopropionic acid,
Dab, Diaminobutyric acid.

Note also that the dipeptide conjugates mentioned above according to this invention are obtained in the terminal form $NH_2$ (in other words they present an amide function).

Dipeptide conjugates according to this invention are bonded to acid with formula II in the form of salts or esters. The conjugations according to this invention may be made by making the acid function of the amino acid react with the acid function of the formula II acid, or it is even possible to take advantage of the presence of a hydroxyl function on the formula II acid.

This invention relates to all these conjugations and non-functional conjugates. Conjugations may be physical or chemical.

Advantageously, at least one of the amino acids AA2 or AA1, and advantageously both of them, represent a basic amino acid, advantageously selected from the group consisting of Arg, His, Dap, Dab, Orn or Lys, advantageously it will be Arg.

Advantageously, AA2 represents a basic amino acid advantageously selected from the group consisting of Arg, His, Lys, Orn, Dap, Dab, advantageously it is Arg.

Advantageously, AA1 and/or AA2 do not represent Trp.

Advantageously, AA1 and/or AA2 do not represent Cys.

Advantageously, at least one of the amino acids AA1 or AA2 is selected from the group consisting of Ser and Pro.

Advantageously AA1 represents Pro.

Advantageously AA2 represents Ser.

Advantageously, the acid with formula (II) is a polyunsaturated fatty acid, in other words it comprises between 1 and 6 unsaturations. Even more advantageously, it is an omega-3 acid.

Among these omega-3 acids, there is particularly α-linolenic acid, cervonic acid, timnodonic acid and pinolenic acid. Cervonic, timnodonic and pinolenic acids are also known under the names 4,7,10,13,16,19-docosahexaenoic acid (DHA), 5,8,11,14,17-eicosapentaenoic acid (EPA) and 5,9,12-octodecatrienoic acid, respectively.

When A represents a monocarboxylic acid radical with general formula (II), it may advantageously be selected from among acetic acid, myristic acid, palmitic acid, hydroxydecenoic and decenoic acid, and particularly trans-10-hydroxy-Δ2-decenoic acid and trans-oxo-9-decene-2-oic acid.

Advantageously, acid with formula (II) is an acid selected from among lipoic acid (Lip) or its reduced form dihydrolipoic acid, N-lipoyllysine or phenylbutyric acid (Pbu).

Advantageously, A represents the radical corresponding to palmitic acid (Palm).

The dipeptide conjugates of the invention include the dipeptide conjugates selected from among the group consisting of:
a) A-Arg-His-NH$_2$,
b) A-Arg-Arg-NH$_2$,
c) A-Arg-Pro-NH$_2$,
d) A-Arg-Lys-NH$_2$,
e) A-Ser-Pro-NH$_2$,
f) A-DPhe-Arg-NH$_2$,
in which the definition of A is as given above.

In particular, the dipeptide conjugates in the invention may be selected from among the group consisting of
39) Palm-Arg-His-NH$_2$,
41) Palm-Arg-Arg-NH$_2$,
49) Palm-Arg-Pro-NH$_2$,
50) Palm-Arg-Lys-NH$_2$,
125) Palm-Ser-Pro-NH$_2$,
269) Palm-DPhe-Arg-NH$_2$,
362) Pbu-DPhe-Arg-NH$_2$,
363) Lip-DPhe-Arg-NH$_2$ Dipeptide conjugates according to this invention may be obtained either advantageously by classical chemical synthesis, or by enzymatic synthesis using any processes known to those skilled in the art.

This invention also relates to a cosmetic, dermatological or pharmaceutical composition or a food supplement comprising a dipeptide conjugate according to this invention and possibly a cosmetically or pharmaceutically acceptable excipient.

Dipeptide conjugates can be administered for their cosmetic or pharmaceutical use by topical route. They can also be used orally in food supplements, in other words in the nutraceutical domain.

Dipeptide conjugates according to the invention are preferably administered topically.

The cosmetic, pharmaceutical or dermatological composition according to this invention intended for topical administration may be presented in forms that are normally known for this type of administration, in other words particularly lotions, foams, gels, dispersions, sprays, serums, masks, body milk, pomades, solutions, emulsions, gels, or creams for example with excipients particularly for skin penetration in order to improve the properties and accessibility of the active ingredient. These compositions usually also contain the dipeptide conjugate according to this invention and usually also a physiologically acceptable medium, usually based on water or solvent, for example alcohols, ethers or glycols. They can also contain surface active agents, preservatives, stabilizers, emulsifiers, thickeners, other active constituents leading to a complementary or possibly synergic effect, trace elements, essential oils, perfumes, coloring agents, collagen, chemical or mineral filters, moisturizers or thermal water.

In the composition according to this invention, the dipeptide conjugate according to the invention may be present at a concentration of between $10^{-8}$ M and $10^{-3}$ M, advantageously between $10^{-7}$ M and $10^{-5}$ M.

This invention also relates to a dipeptide conjugate according to this invention or a pharmaceutical composition according to this invention for its use as a medicine, advantageously designed to prevent, improve or treat immunitary abnormalities, immunodeficiency, to regulate the body weight by controlling the appetite, to treat disorders of the central nervous system, to regulate satiety, to treat anorexia or some skin cancers.

This invention also relates to the use of a cosmetic composition according to this invention as a depigmenting agent to lighten or whiten the epidermis, to eliminate skin spots, particularly age spots or freckles, or to prevent pigmentation of the epidermis.

Finally, this invention relates to a cosmetic treatment process to lighten, depigment or whiten the epidermis, to eliminate skin spots and particularly age spots or freckles, or prevent pigmentation of the epidermis including application of a cosmetic composition according to this invention to the skin.

The following examples are given for non-limitative guidance.

EXAMPLE 1

Preparation of 361 Dipeptides According to the Invention

A bank of acylated dipeptides with 361 members was synthesized using SynPhase™ Lanterns and a "split and pool" strategy for color marking as described in the article by Feliu et al. (J. Comb. Chem., 2003, 5, pages 256-361).

Thus, these 361 compounds were synthesized on series D SynPhase™ Lanterns with Rink amide PS resin using the standard Fmoc (9-fluorenyl-methoxycarbonyl) synthesis strategy in the solid phase using a Multipin 96 arrangement format. Component blocks AA1 and AA2 were selected from a chemical assembly of 19 D and L amino acids including several types of lateral chains (alkyl, aromatic, acid, voluminous, basic) to produce 19×19=361 combinations.

The following chemical products were used:

Amino acids protected at the N-terminal end by an α-Fmoc, Fmoc-Ala-OH, Fmoc-D-Ala-OH, Fmoc-Arg(Pbf)-OH, Fmoc-D-Arg-(Pbf)-OH, Fmoc-His(Trt)-OH, Fmoc-D-His(Trt)-OH, Fmoc-Lys(Boc)-OH, Fmoc-Phe-OH, Fmoc-D-Phe-OH, Fmoc-Trp(Boc)-OH, Fmoc-D-Trp(Boc)-OH, Fmoc-Met-OH, Fmoc-Glu(OtBu)-OH, Fmoc-Ser(tBu)-OH, Fmoc-Leu-OH, Fmoc-Tyr(tBu)-OH, Fmoc-Gly-OH, Fmoc-Pro-OH, or Fmoc-Asn(trt)-OH group, were purchased from SENN chemicals and Advanced Chemtech.

The coupling agent, HBTU (hexafluorophosphate of 2-(1-H-benzotriazol-1-yl)-1,1,3,3-tetramethyl-uronium), was purchased from SENN chemicals.

N,N-dimethylformamide (DMF), dichloromethane, methanol, acetonitrile, ethyl ether, trifluoroacetic acid (TFA), piperidine were purchased from Riedel de Haen, Carlo Erba or Acros organics and used without purification.

N,N-diisopropylethylamine (DIEA), triisopropyl-silane, palmitic acid were purchased from Aldrich or Avocado. All reagents and chemical products were of analytic quality and they were used without any other purification.

D series Synphase Polystyrene Rink amide Lanterns were supplied by Mimotopes, Pty.

The standard procedure for manufacturing these dipeptides includes the following steps:

1—Fmoc Standard Deprotection Protocol

Fmoc deprotection steps were done by immersing lanterns immobilized on a support of 96 rods in a mix of dimethylsulfoxide (DMF)/piperidine (80/20, v/v) for 30 minutes. Rectangular polypropylene receptacles of the same size as a standard plate with 96 wells were used. The excess deprotection solution was simply eliminated by stirring the rod support vigorously.

2—Standard Washing Protocol

After the coupling or deprotection step, washing steps were carried out by dipping the lanterns arranged in a Multipin format into polypropylene receptacles containing DMF (3×5 min), methanol (2×5 min) and dichloromethane (DCM) (1×5 min), all in sequence. The lanterns were dried in air for 5 minutes under a vapor hood after the last washing with DCM.

3—Standard Coupling Protocol 0.4 M solutions of each Fmoc amino acid, HBTU and DIEA were prepared in DMF and were kept at 4° C. throughout the synthesis. 200 µl of amino acid solution were distributed in plates with 96 deep wells. 200 µl of DIEA solution and 200 µl of HBTU solution were then added and finally, the support of the rods supporting the lanterns was adapted to the deep wells plate for 2 hours.

4—Cleavage

500 µl of TFA/water/triisopropylsilane (95/2.5/2.5, v/v/v) solution was distributed in individual polypropylene tubes arranged in Micronic plates with 96 wells. Cleavage was done for 3 hours. The cleavage cocktail was concentrated directly from plates using a Jouan RC1010 vacuum centrifuge. Compounds were precipitated with dry diethyl ether, and were centrifuged and settled one by one. Precipitation, centrifuging and settlement operations were repeated twice. 500 µl of acetonitrile/water (50/50, v/v) containing 0.1% of TFA were distributed in each tube to solubilize the samples. The samples were then frozen at −80° C. and freeze dried. This operation was repeated twice to completely eliminate the triisopropylsilane purification group.

5—Preparation and Analysis of Samples

Complete banks and simple re-synthesized peptides were analyzed by CLHP in inverse phase and CL/SM. 500 µl of acetonitrile/water (50/50, v/v) containing 0.1% of TFA were distributed on the freeze-dried compounds. 10 µl of each tube was sampled for analysis of CLHP and CL/SM ESI+.

The CLHP analyses were carried out on a CLHP Waters Alliance 2690 system and a Waters 996 photodiode strip detector and a 50×4.6 mm Merck Chromolith Speed ROD C18 column. A flow rate of 5 ml/min and a gradient from 100% of B to 100% of C was used over 3 minutes (Eluant B, water/0.1% of TFA; Eluant C, acetonitrile/0.1% of TFA). Estimates of the purity are based on the percent of the area of peaks detected at 214 nm.

The CL/SM system was composed of a Waters Alliance 2690 CLHP coupled to a Micromass Platform II spectrometer (ionization by electronebulization mode; ESI+). All analyses were done using a 2.1×30 mm Waters Symmetry C18 column, 3.5 µm. A 600 µl/min flow rate and a gradient from 100% of B to 100% of C over 3 minutes were used (Eluant B, water/0.1% of TFA; Eluant C, acetonitrile/0.1% of TFA).

Mass spectra by positive ionic electronebulization were acquired at a solvent flow rate of 100 ml/min. Nitrogen was used both for the nebulizing gas and for the drying gas. Data were acquired in read mode m/z 400 to 1400 at intervals of $0.1^{-s}$; 10 readings were added to produce the final spectrum.

The molecular weights of all compounds were calculated using mono-isotopic masses (C=12.000, H=1.007, N=14.003, O=15.994, S=31.972).

Table 1 below contains the analysis results.

TABLE 1

Analytic results of the Palm-dipeptides bank

| Dipeptide conjugate number according to the invention | Sequence | | | | % purity | Molecular weight |
|---|---|---|---|---|---|---|
| | A | AA2 | AA1 | | | |
| 1 | Palm | His | His | $NH_2$ | 97 | 529.3 |
| 2 | Palm | His | Phe | $NH_2$ | 100 | 539.4 |
| 3 | Palm | His | Arg | $NH_2$ | 100 | 548.4 |
| 4 | Palm | His | Trp | $NH_2$ | 89 | 578.4 |
| 5 | Palm | His | Glu | $NH_2$ | 100 | 521.3 |
| 6 | Palm | His | Ala | $NH_2$ | 100 | 463.3 |
| 7 | Palm | His | Ser | $NH_2$ | 100 | 479.3 |
| 8 | Palm | His | Leu | $NH_2$ | 100 | 505.4 |
| 9 | Palm | His | Tyr | $NH_2$ | 100 | 555.3 |
| 10 | Palm | His | Gly | $NH_2$ | 96 | 449.3 |
| 11 | Palm | His | Pro | $NH_2$ | 100 | 489.3 |
| 12 | Palm | His | Lys | $NH_2$ | 100 | 520.4 |
| 13 | Palm | His | Asn | $NH_2$ | 100 | 506.3 |
| 14 | Palm | His | Met | $NH_2$ | 88 | 523.3 |
| 15 | Palm | His | DPhe | $NH_2$ | 81 | 539.4 |
| 16 | Palm | His | DTrp | $NH_2$ | 88 | 578.4 |
| 17 | Palm | His | DArg | $NH_2$ | 100 | 548.4 |
| 18 | Palm | His | DHis | $NH_2$ | 97 | 529.3 |
| 19 | Palm | His | DAla | $NH_2$ | 88 | 463.3 |
| 20 | Palm | Phe | His | $NH_2$ | 100 | 539.4 |
| 21 | Palm | Phe | Phe | $NH_2$ | — | — |
| 22 | Palm | Phe | Arg | $NH_2$ | 100 | 558.4 |
| 23 | Palm | Phe | Trp | $NH_2$ | 100 | 588.4 |
| 24 | Palm | Phe | Glu | $NH_2$ | 100 | 531.3 |
| 25 | Palm | Phe | Ala | $NH_2$ | 100 | 473.3 |
| 26 | Palm | Phe | Ser | $NH_2$ | 100 | 489.3 |
| 27 | Palm | Phe | Leu | $NH_2$ | — | — |
| 28 | Palm | Phe | Tyr | $NH_2$ | 100 | 565.4 |
| 29 | Palm | Phe | Gly | $NH_2$ | 100 | 459.3 |
| 30 | Palm | Phe | Pro | $NH_2$ | 23 | 499.35 |
| 31 | Palm | Phe | Lys | $NH_2$ | 100 | 530.4 |
| 32 | Palm | Phe | Asn | $NH_2$ | 80 | 516.3 |
| 33 | Palm | Phe | Met | $NH_2$ | 100 | 533.3 |

TABLE 1-continued

Analytic results of the Palm-dipeptides bank

| Dipeptide conjugate number according to the invention | A | AA2 | AA1 | | % purity | Molecular weight |
|---|---|---|---|---|---|---|
| 34 | Palm | Phe | DPhe | NH$_2$ | 100 | 549.4 |
| 35 | Palm | Phe | DTrp | NH$_2$ | | |
| 36 | Palm | Phe | DArg | NH$_2$ | 100 | 558.4 |
| 37 | Palm | Phe | DHis | NH$_2$ | 96 | 539.4 |
| 38 | Palm | Phe | DAla | NH$_2$ | 100 | 473.3 |
| 39 | Palm | Arg | His | NH$_2$ | 94 | 548.4 |
| 40 | Palm | Arg | Phe | NH$_2$ | 100 | 558.4 |
| 41 | Palm | Arg | Arg | NH$_2$ | 100 | 567.4 |
| 42 | Palm | Arg | Trp | NH$_2$ | 95 | 597.4 |
| 43 | Palm | Arg | Glu | NH$_2$ | 100 | 540.4 |
| 44 | Palm | Arg | Ala | NH$_2$ | 94 | 482.4 |
| 45 | Palm | Arg | Ser | NH$_2$ | 100 | 498.4 |
| 46 | Palm | Arg | Leu | NH$_2$ | 100 | 524.4 |
| 47 | Palm | Arg | Tyr | NH$_2$ | 93 | 574.4 |
| 48 | Palm | Arg | Gly | NH$_2$ | 100 | 468.3 |
| 49 | Palm | Arg | Pro | NH$_2$ | 87 | 508.4 |
| 50 | Palm | Arg | Lys | NH$_2$ | 100 | 539.4 |
| 51 | Palm | Arg | Asn | NH$_2$ | 91 | 525.4 |
| 52 | Palm | Arg | Met | NH$_2$ | 100 | 542.4 |
| 53 | Palm | Arg | DPhe | NH$_2$ | 100 | 558.4 |
| 54 | Palm | Arg | DTrp | NH$_2$ | 60 | 597.4 |
| 55 | Palm | Arg | DArg | NH$_2$ | 100 | 567.4 |
| 56 | Palm | Arg | DHis | NH$_2$ | 100 | 548.4 |
| 57 | Palm | Arg | DAla | NH$_2$ | 100 | 482.4 |
| 58 | Palm | Trp | His | NH$_2$ | 93 | 578.4 |
| 59 | Palm | Trp | Phe | NH$_2$ | 100 | 588.4 |
| 60 | Palm | Trp | Arg | NH$_2$ | 100 | 597.4 |
| 61 | Palm | Trp | Trp | NH$_2$ | | |
| 62 | Palm | Trp | Glu | NH$_2$ | 87 | 570.3 |
| 63 | Palm | Trp | Ala | NH$_2$ | 89 | 512.3 |
| 64 | Palm | Trp | Ser | NH$_2$ | 89 | 528.3 |
| 65 | Palm | Trp | Leu | NH$_2$ | | |
| 66 | Palm | Trp | Tyr | NH$_2$ | 90 | 604.4 |
| 67 | Palm | Trp | Gly | NH$_2$ | 90 | 498.3 |
| 68 | Palm | Trp | Pro | NH$_2$ | 100 | 538.4 |
| 69 | Palm | Trp | Lys | NH$_2$ | 99 | 569.4 |
| 70 | Palm | Trp | Asn | NH$_2$ | 95 | 555.3 |
| 71 | Palm | Trp | Met | NH$_2$ | 89 | 572.3 |
| 72 | Palm | Trp | DPhe | NH$_2$ | | |
| 73 | Palm | Trp | DTrp | NH$_2$ | 76 | 627.4 |
| 74 | Palm | Trp | DArg | NH$_2$ | 93 | 597.4 |
| 75 | Palm | Trp | DHis | NH$_2$ | 79 | 578.4 |
| 76 | Palm | Trp | DAla | NH$_2$ | 100 | 512.3 |
| 77 | Palm | Glu | His | NH$_2$ | 94 | 521.3 |
| 78 | Palm | Glu | Phe | NH$_2$ | 100 | 531.3 |
| 79 | Palm | Glu | Arg | NH$_2$ | 100 | 540.4 |
| 80 | Palm | Glu | Trp | NH$_2$ | 82 | 570.3 |
| 81 | Palm | Glu | Glu | NH$_2$ | 100 | 513.3 |
| 82 | Palm | Glu | Ala | NH$_2$ | 100 | 455.3 |
| 83 | Palm | Glu | Ser | NH$_2$ | 100 | 471.3 |
| 84 | Palm | Glu | Leu | NH$_2$ | 100 | 497.4 |
| 85 | Palm | Glu | Tyr | NH$_2$ | 100 | 547.3 |
| 86 | Palm | Glu | Gly | NH$_2$ | 100 | 441.3 |
| 87 | Palm | Glu | Pro | NH$_2$ | 10 | 481.32 |
| 88 | Palm | Glu | Lys | NH$_2$ | 100 | 512.4 |
| 89 | Palm | Glu | Asn | NH$_2$ | 7 | 498.31 |
| 90 | Palm | Glu | Met | NH$_2$ | 100 | 515.3 |
| 91 | Palm | Glu | DPhe | NH$_2$ | 100 | 531.3 |
| 92 | Palm | Glu | DTrp | NH$_2$ | | |
| 93 | Palm | Glu | DArg | NH$_2$ | 100 | 540.4 |
| 94 | Palm | Glu | DHis | NH$_2$ | 100 | 521.3 |
| 95 | Palm | Glu | DAla | NH$_2$ | 100 | 455.3 |
| 96 | Palm | Ala | His | NH$_2$ | 97 | 463.3 |
| 97 | Palm | Ala | Phe | NH$_2$ | 94 | 473.3 |
| 98 | Palm | Ala | Arg | NH$_2$ | 100 | 482.4 |
| 99 | Palm | Ala | Trp | NH$_2$ | 98 | 512.3 |
| 100 | Palm | Ala | Glu | NH$_2$ | 100 | 455.3 |
| 101 | Palm | Ala | Ala | NH$_2$ | 100 | 397.3 |
| 102 | Palm | Ala | Ser | NH$_2$ | 100 | 413.3 |
| 103 | Palm | Ala | Leu | NH$_2$ | 100 | 439.3 |
| 104 | Palm | Ala | Tyr | NH$_2$ | 100 | 489.3 |
| 105 | Palm | Ala | Gly | NH$_2$ | 100 | 383.3 |
| 106 | Palm | Ala | Pro | NH$_2$ | 100 | 423.3 |
| 107 | Palm | Ala | Lys | NH$_2$ | 100 | 454.4 |
| 108 | Palm | Ala | Asn | NH$_2$ | 100 | 440.3 |
| 109 | Palm | Ala | Met | NH$_2$ | 100 | 457.3 |
| 110 | Palm | Ala | DPhe | NH$_2$ | 100 | 473.3 |
| 111 | Palm | Ala | DTrp | NH$_2$ | 96 | 512.3 |
| 112 | Palm | Ala | DArg | NH$_2$ | 100 | 482.4 |
| 113 | Palm | Ala | DHis | NH$_2$ | 84 | 463.3 |
| 114 | Palm | Ala | DAla | NH$_2$ | 100 | 397.3 |
| 115 | Palm | Ser | His | NH$_2$ | 95 | 479.3 |
| 116 | Palm | Ser | Phe | NH$_2$ | 100 | 489.3 |
| 117 | Palm | Ser | Arg | NH$_2$ | 100 | 498.4 |
| 118 | Palm | Ser | Trp | NH$_2$ | 96 | 528.3 |
| 119 | Palm | Ser | Glu | NH$_2$ | 100 | 471.3 |
| 120 | Palm | Ser | Ala | NH$_2$ | 100 | 413.3 |
| 121 | Palm | Ser | Ser | NH$_2$ | 100 | 429.3 |
| 122 | Palm | Ser | Leu | NH$_2$ | 100 | 455.3 |
| 123 | Palm | Ser | Tyr | NH$_2$ | 97 | 505.3 |
| 124 | Palm | Ser | Gly | NH$_2$ | 100 | 399.3 |
| 125 | Palm | Ser | Pro | NH$_2$ | 100 | 439.3 |
| 126 | Palm | Ser | Lys | NH$_2$ | 100 | 470.4 |
| 127 | Palm | Ser | Asn | NH$_2$ | 32 | 456.3 |
| 128 | Palm | Ser | Met | NH$_2$ | 50 | 473.3 |
| 129 | Palm | Ser | DPhe | NH$_2$ | 100 | 489.3 |
| 130 | Palm | Ser | DTrp | NH$_2$ | 93 | 528.3 |
| 131 | Palm | Ser | DArg | NH$_2$ | 0 | 498.4 |
| 132 | Palm | Ser | DHis | NH$_2$ | 91 | 479.3 |
| 133 | Palm | Ser | DAla | NH$_2$ | 100 | 413.3 |
| 134 | Palm | Leu | His | NH$_2$ | 92 | 505.4 |
| 135 | Palm | Leu | Phe | NH$_2$ | 100 | 515.4 |
| 136 | Palm | Leu | Arg | NH$_2$ | 100 | 524.4 |
| 137 | Palm | Leu | Trp | NH$_2$ | 100 | 554.4 |
| 138 | Palm | Leu | Glu | NH$_2$ | 100 | 497.4 |
| 139 | Palm | Leu | Ala | NH$_2$ | 100 | 439.3 |
| 140 | Palm | Leu | Ser | NH$_2$ | 100 | 455.3 |
| 141 | Palm | Leu | Leu | NH$_2$ | 100 | 481.4 |
| 142 | Palm | Leu | Tyr | NH$_2$ | 100 | 531.4 |
| 143 | Palm | Leu | Gly | NH$_2$ | 100 | 425.3 |
| 144 | Palm | Leu | Pro | NH$_2$ | | |
| 145 | Palm | Leu | Lys | NH$_2$ | 100 | 496.4 |
| 146 | Palm | Leu | Asn | NH$_2$ | 15 | 482.4 |
| 147 | Palm | Leu | Met | NH$_2$ | 100 | 499.3 |
| 148 | Palm | Leu | DPhe | NH$_2$ | 100 | 515.4 |
| 149 | Palm | Leu | DTrp | NH$_2$ | 87 | 554.4 |
| 150 | Palm | Leu | DArg | NH$_2$ | 100 | 524.4 |
| 151 | Palm | Leu | DHis | NH$_2$ | 86 | 505.4 |
| 152 | Palm | Leu | DAla | NH$_2$ | 100 | 439.3 |
| 153 | Palm | Tyr | His | NH$_2$ | 96 | 555.3 |
| 154 | Palm | Tyr | Phe | NH$_2$ | | |
| 155 | Palm | Tyr | Arg | NH$_2$ | 87 | 574.4 |
| 156 | Palm | Tyr | Trp | NH$_2$ | 78 | 604.4 |
| 157 | Palm | Tyr | Glu | NH$_2$ | 100 | 547.3 |
| 158 | Palm | Tyr | Ala | NH$_2$ | 100 | 489.3 |
| 159 | Palm | Tyr | Ser | NH$_2$ | 100 | 505.3 |
| 160 | Palm | Tyr | Leu | NH$_2$ | 100 | 531.4 |
| 161 | Palm | Tyr | Tyr | NH$_2$ | 98 | 581.4 |
| 162 | Palm | Tyr | Gly | NH$_2$ | 100 | 475.3 |
| 163 | Palm | Tyr | Pro | NH$_2$ | 93 | 515.3 |
| 164 | Palm | Tyr | Lys | NH$_2$ | 100 | 546.4 |

TABLE 1-continued

Analytic results of the Palm-dipeptides bank

| Dipeptide conjugate number according to the invention | A | AA2 | AA1 | | % purity | Molecular weight |
|---|---|---|---|---|---|---|
| 165 | Palm | Tyr | Asn | NH$_2$ | 100 | 532.3 |
| 166 | Palm | Tyr | Met | NH$_2$ | | |
| 167 | Palm | Tyr | DPhe | NH$_2$ | 87 | 565.4 |
| 168 | Palm | Tyr | DTrp | NH$_2$ | | |
| 169 | Palm | Tyr | DArg | NH$_2$ | 90 | 574.4 |
| 170 | Palm | Tyr | DHis | NH$_2$ | 92 | 555.3 |
| 171 | Palm | Tyr | DAla | NH$_2$ | 100 | 489.3 |
| 172 | Palm | Gly | His | NH$_2$ | 81 | 449.3 |
| 173 | Palm | Gly | Phe | NH$_2$ | 100 | 459.3 |
| 174 | Palm | Gly | Arg | NH$_2$ | 100 | 468.3 |
| 175 | Palm | Gly | Trp | NH$_2$ | 95 | 498.3 |
| 176 | Palm | Gly | Glu | NH$_2$ | 100 | 441.3 |
| 177 | Palm | Gly | Ala | NH$_2$ | 100 | 383.3 |
| 178 | Palm | Gly | Ser | NH$_2$ | 100 | 399.3 |
| 179 | Palm | Gly | Leu | NH$_2$ | | |
| 180 | Palm | Gly | Tyr | NH$_2$ | 100 | 475.3 |
| 181 | Palm | Gly | Gly | NH$_2$ | 100 | 369.3 |
| 182 | Palm | Gly | Pro | NH$_2$ | 100 | 409.3 |
| 183 | Palm | Gly | Lys | NH$_2$ | 81 | 440.3 |
| 184 | Palm | Gly | Asn | NH$_2$ | 57 | 426.3 |
| 185 | Palm | Gly | Met | NH$_2$ | 100 | 443.3 |
| 186 | Palm | Gly | DPhe | NH$_2$ | 100 | 459.3 |
| 187 | Palm | Gly | DTrp | NH$_2$ | 68 | 498.3 |
| 188 | Palm | Gly | DArg | NH$_2$ | 100 | 468.3 |
| 189 | Palm | Gly | DHis | NH$_2$ | 90 | 449.3 |
| 190 | Palm | Gly | DAla | NH$_2$ | 100 | 383.3 |
| 191 | Palm | Pro | His | NH$_2$ | 97 | 489.34 |
| 192 | Palm | Pro | Phe | NH$_2$ | 97 | 499.35 |
| 193 | Palm | Pro | Arg | NH$_2$ | | |
| 194 | Palm | Pro | Trp | NH$_2$ | | |
| 195 | Palm | Pro | Glu | NH$_2$ | | |
| 196 | Palm | Pro | Ala | NH$_2$ | | |
| 197 | Palm | Pro | Ser | NH$_2$ | 99 | 439.31 |
| 198 | Palm | Pro | Leu | NH$_2$ | 72 | 465.36 |
| 199 | Palm | Pro | Tyr | NH$_2$ | 98 | 515.34 |
| 200 | Palm | Pro | Gly | NH$_2$ | 24 | 409.30 |
| 201 | Palm | Pro | Pro | NH$_2$ | 78 | 449.33 |
| 202 | Palm | Pro | Lys | NH$_2$ | 93 | 480.37 |
| 203 | Palm | Pro | Asn | NH$_2$ | 97 | 466.32 |
| 204 | Palm | Pro | Met | NH$_2$ | 97 | 483.32 |
| 205 | Palm | Pro | DPhe | NH$_2$ | 22 | 499.35 |
| 206 | Palm | Pro | DTrp | NH$_2$ | 96 | 538.36 |
| 207 | Palm | Pro | DArg | NH$_2$ | 37 | 508.38 |
| 208 | Palm | Pro | DHis | NH$_2$ | 73 | 489.34 |
| 209 | Palm | Pro | DAla | NH$_2$ | 59 | 423.32 |
| 210 | Palm | Lys | His | NH$_2$ | 92 | 520.38 |
| 211 | Palm | Lys | Phe | NH$_2$ | | |
| 212 | Palm | Lys | Arg | NH$_2$ | 73 | 539.42 |
| 213 | Palm | Lys | Trp | NH$_2$ | 92 | 569.40 |
| 214 | Palm | Lys | Glu | NH$_2$ | 90 | 512.36 |
| 215 | Palm | Lys | Ala | NH$_2$ | 87 | 454.36 |
| 216 | Palm | Lys | Ser | NH$_2$ | 86 | 470.35 |
| 217 | Palm | Lys | Leu | NH$_2$ | 80 | 496.40 |
| 218 | Palm | Lys | Tyr | NH$_2$ | 97 | 546.38 |
| 219 | Palm | Lys | Gly | NH$_2$ | 89 | 440.34 |
| 220 | Palm | Lys | Pro | NH$_2$ | 21 | 480.37 |
| 221 | Palm | Lys | Lys | NH$_2$ | 96 | 511.41 |
| 222 | Palm | Lys | Asn | NH$_2$ | | |
| 223 | Palm | Lys | Met | NH$_2$ | 89 | 514.36 |
| 224 | Palm | Lys | DPhe | NH$_2$ | 95 | 530.39 |
| 225 | Palm | Lys | DTrp | NH$_2$ | 92 | 569.40 |
| 226 | Palm | Lys | DArg | NH$_2$ | 94 | 539.42 |
| 227 | Palm | Lys | DHis | NH$_2$ | 94 | 520.38 |
| 228 | Palm | Lys | DAla | NH$_2$ | 83 | 454.36 |
| 229 | Palm | Asn | His | NH$_2$ | 28 | 506.33 |
| 230 | Palm | Asn | Phe | NH$_2$ | | |
| 231 | Palm | Asn | Arg | NH$_2$ | 42 | 525.37 |
| 232 | Palm | Asn | Trp | NH$_2$ | 88 | 555.35 |
| 233 | Palm | Asn | Glu | NH$_2$ | | |
| 234 | Palm | Asn | Ala | NH$_2$ | 80 | 440.31 |
| 235 | Palm | Asn | Ser | NH$_2$ | | |
| 236 | Palm | Asn | Leu | NH$_2$ | | |
| 237 | Palm | Asn | Tyr | NH$_2$ | | |
| 238 | Palm | Asn | Gly | NH$_2$ | 32 | 426.30 |
| 239 | Palm | Asn | Pro | NH$_2$ | 89 | 466.32 |
| 240 | Palm | Asn | Lys | NH$_2$ | 30 | 497.36 |
| 241 | Palm | Asn | Asn | NH$_2$ | 85 | 483.31 |
| 242 | Palm | Asn | Met | NH$_2$ | 77 | 500.31 |
| 243 | Palm | Asn | DPhe | NH$_2$ | 76 | 516.34 |
| 244 | Palm | Asn | DTrp | NH$_2$ | 57 | 555.35 |
| 245 | Palm | Asn | DArg | NH$_2$ | | |
| 246 | Palm | Asn | DHis | NH$_2$ | | |
| 247 | Palm | Asn | DAla | NH$_2$ | 95 | 440.31 |
| 248 | Palm | Met | His | NH$_2$ | 85 | 523.33 |
| 249 | Palm | Met | Phe | NH$_2$ | 84 | 533.33 |
| 250 | Palm | Met | Arg | NH$_2$ | 76 | 542.37 |
| 251 | Palm | Met | Trp | NH$_2$ | 85 | 572.34 |
| 252 | Palm | Met | Glu | NH$_2$ | 87 | 515.31 |
| 253 | Palm | Met | Ala | NH$_2$ | 99 | 457.31 |
| 254 | Palm | Met | Ser | NH$_2$ | 55 | 473.30 |
| 255 | Palm | Met | Leu | NH$_2$ | 78 | 499.35 |
| 256 | Palm | Met | Tyr | NH$_2$ | 80 | 549.33 |
| 257 | Palm | Met | Gly | NH$_2$ | 63 | 443.29 |
| 258 | Palm | Met | Pro | NH$_2$ | 85 | 483.32 |
| 259 | Palm | Met | Lys | NH$_2$ | 88 | 514.36 |
| 260 | Palm | Met | Asn | NH$_2$ | 92 | 500.31 |
| 261 | Palm | Met | Met | NH$_2$ | 85 | 517.31 |
| 262 | Palm | Met | DPhe | NH$_2$ | 91 | 533.33 |
| 263 | Palm | Met | DTrp | NH$_2$ | 78 | 572.34 |
| 264 | Palm | Met | DArg | NH$_2$ | 57 | 542.37 |
| 265 | Palm | Met | DHis | NH$_2$ | 86 | 523.33 |
| 266 | Palm | Met | DAla | NH$_2$ | 31 | 457.31 |
| 267 | Palm | DPhe | His | NH$_2$ | 95 | 539.35 |
| 268 | Palm | DPhe | Phe | NH$_2$ | 76 | 549.36 |
| 269 | Palm | DPhe | Arg | NH$_2$ | 85 | 558.39 |
| 270 | Palm | DPhe | Trp | NH$_2$ | 70 | 588.37 |
| 271 | Palm | DPhe | Glu | NH$_2$ | 33 | 531.34 |
| 272 | Palm | DPhe | Ala | NH$_2$ | 97 | 473.33 |
| 273 | Palm | DPhe | Ser | NH$_2$ | 83 | 489.33 |
| 274 | Palm | DPhe | Leu | NH$_2$ | 79 | 515.38 |
| 275 | Palm | DPhe | Tyr | NH$_2$ | 93 | 565.36 |
| 276 | Palm | DPhe | Gly | NH$_2$ | 88 | 459.32 |
| 277 | Palm | DPhe | Pro | NH$_2$ | 50 | 499.35 |
| 278 | Palm | DPhe | Lys | NH$_2$ | 65 | 530.39 |
| 279 | Palm | DPhe | Asn | NH$_2$ | 77 | 516.34 |
| 280 | Palm | DPhe | Met | NH$_2$ | 97 | 533.33 |
| 281 | Palm | DPhe | DPhe | NH$_2$ | 76 | 549.36 |
| 282 | Palm | DPhe | DTrp | NH$_2$ | 87 | 588.37 |
| 283 | Palm | DPhe | DArg | NH$_2$ | 92 | 558.39 |
| 284 | Palm | DPhe | DHis | NH$_2$ | 96 | 539.35 |
| 285 | Palm | DPhe | DAla | NH$_2$ | 78 | 473.33 |
| 286 | Palm | DTrp | His | NH$_2$ | 69 | 578.36 |

TABLE 1-continued

Analytic results of the Palm-dipeptides bank

| Dipeptide conjugate number according to the invention | A | AA2 | AA1 | | % purity | Molecular weight |
|---|---|---|---|---|---|---|
| 287 | Palm | DTrp | Phe | $NH_2$ | 82 | 578.36 |
| 288 | Palm | DTrp | Arg | $NH_2$ | 79 | 588.37 |
| 289 | Palm | DTrp | Trp | $NH_2$ | 46 | 597.40 |
| 290 | Palm | DTrp | Glu | $NH_2$ | 71 | 627.38 |
| 291 | Palm | DTrp | Ala | $NH_2$ | 60 | 570.35 |
| 292 | Palm | DTrp | Ser | $NH_2$ | | |
| 293 | Palm | DTrp | Leu | $NH_2$ | 37 | 528.34 |
| 294 | Palm | DTrp | Tyr | $NH_2$ | 68 | 554.39 |
| 295 | Palm | DTrp | Gly | $NH_2$ | 69 | 604.37 |
| 296 | Palm | DTrp | Pro | $NH_2$ | 72 | 498.33 |
| 297 | Palm | DTrp | Lys | $NH_2$ | 96 | 538.36 |
| 298 | Palm | DTrp | Asn | $NH_2$ | 84 | 569.40 |
| 299 | Palm | DTrp | Met | $NH_2$ | 60 | 555.35 |
| 300 | Palm | DTrp | DPhe | $NH_2$ | 70 | 572.34 |
| 301 | Palm | DTrp | DTrp | $NH_2$ | 52 | 588.37 |
| 302 | Palm | DTrp | DArg | $NH_2$ | 86 | 627.38 |
| 303 | Palm | DTrp | DHis | $NH_2$ | 95 | 597.40 |
| 304 | Palm | DTrp | DAla | $NH_2$ | | |
| 305 | Palm | DArg | His | $NH_2$ | | |
| 306 | Palm | DArg | Phe | $NH_2$ | 42 | 548.38 |
| 307 | Palm | DArg | Arg | $NH_2$ | 60 | 558.39 |
| 308 | Palm | DArg | Trp | $NH_2$ | 42 | 567.42 |
| 309 | Palm | DArg | Glu | $NH_2$ | 73 | 597.40 |
| 310 | Palm | DArg | Ala | $NH_2$ | 82 | 540.37 |
| 311 | Palm | DArg | Ser | $NH_2$ | 74 | 482.36 |
| 312 | Palm | DArg | Leu | $NH_2$ | 34 | 498.36 |
| 313 | Palm | DArg | Tyr | $NH_2$ | 27 | 524.41 |
| 314 | Palm | DArg | Gly | $NH_2$ | 32 | 574.39 |
| 315 | Palm | DArg | Pro | $NH_2$ | 40 | 468.35 |
| 316 | Palm | DArg | Lys | $NH_2$ | | |
| 317 | Palm | DArg | Asn | $NH_2$ | 40 | 539.42 |
| 318 | Palm | DArg | Met | $NH_2$ | 9 | 525.37 |
| 319 | Palm | DArg | DPhe | $NH_2$ | 82 | 542.37 |
| 320 | Palm | DArg | DTrp | $NH_2$ | 30 | 558.39 |
| 321 | Palm | DArg | DArg | $NH_2$ | 20 | 597.40 |
| 322 | Palm | DArg | DHis | $NH_2$ | 70 | 567.42 |
| 323 | Palm | DArg | DAla | $NH_2$ | 83 | 548.38 |
| 324 | Palm | DHis | His | $NH_2$ | 75 | 482.36 |
| 325 | Palm | DHis | Phe | $NH_2$ | 66 | 529.35 |
| 326 | Palm | DHis | Arg | $NH_2$ | 53 | 539.35 |
| 327 | Palm | DHis | Trp | $NH_2$ | 69 | 548.38 |
| 328 | Palm | DHis | Glu | $NH_2$ | | |
| 329 | Palm | DHis | Ala | $NH_2$ | 63 | 521.33 |
| 330 | Palm | DHis | Ser | $NH_2$ | 47 | 463.32 |
| 331 | Palm | DHis | Leu | $NH_2$ | 66 | 479.32 |
| 332 | Palm | DHis | Tyr | $NH_2$ | 79 | 505.37 |
| 333 | Palm | DHis | Gly | $NH_2$ | 89 | 555.35 |
| 334 | Palm | DHis | Pro | $NH_2$ | 96 | 449.31 |
| 335 | Palm | DHis | Lys | $NH_2$ | 90 | 489.34 |
| 336 | Palm | DHis | Asn | $NH_2$ | 87 | 520.38 |
| 337 | Palm | DHis | Met | $NH_2$ | 76 | 506.33 |
| 338 | Palm | DHis | DPhe | $NH_2$ | 96 | 523.33 |
| 339 | Palm | DHis | DTrp | $NH_2$ | 66 | 539.35 |
| 340 | Palm | DHis | DArg | $NH_2$ | | |
| 341 | Palm | DHis | DHis | $NH_2$ | 84 | 548.38 |
| 342 | Palm | DHis | DAla | $NH_2$ | 52 | 529.35 |
| 343 | Palm | DAla | His | $NH_2$ | 70 | 463.32 |
| 344 | Palm | DAla | Phe | $NH_2$ | | |
| 345 | Palm | DAla | Arg | $NH_2$ | 76 | 473.33 |
| 346 | Palm | DAla | Trp | $NH_2$ | 84 | 482.36 |
| 347 | Palm | DAla | Glu | $NH_2$ | | |
| 348 | Palm | DAla | Ala | $NH_2$ | 53 | 455.31 |
| 349 | Palm | DAla | Ser | $NH_2$ | 11 | 397.30 |
| 350 | Palm | DAla | Leu | $NH_2$ | 78 | 413.30 |
| 351 | Palm | DAla | Tyr | $NH_2$ | 87 | 439.35 |
| 352 | Palm | DAla | Gly | $NH_2$ | | |
| 353 | Palm | DAla | Pro | $NH_2$ | 17 | 383.29 |
| 354 | Palm | DAla | Lys | $NH_2$ | 86 | 423.32 |
| 355 | Palm | DAla | Asn | $NH_2$ | 94 | 454.36 |
| 356 | Palm | DAla | Met | $NH_2$ | 10 | 440.31 |
| 357 | Palm | DAla | DPhe | $NH_2$ | 86 | 457.31 |
| 358 | Palm | DAla | DTrp | $NH_2$ | 85 | 473.33 |
| 359 | Palm | DAla | DArg | $NH_2$ | 36 | 512.34 |
| 360 | Palm | DAla | DHis | $NH_2$ | 96 | 482.36 |
| 361 | Palm | DAla | DAla | $NH_2$ | | |

Except for 35 members of the bank (shown in grey), all compounds were detected by a CL/SM ES+ analysis. The average purity determined based on the percent of the area of the expected peak detected at 214 nm on the chromatogram is greater than 83%.

EXAMPLE 2

Biological Properties of Five Dipeptide Conjugates According to this Invention Experiments on inhibition of AMPc production were carried out on the M4Be human cell line with a concentration of $5\times10^{-8}$ M of α-MSH. Five Palm-dipeptides according to this invention were introduced at different concentrations and each measurement was made in triplicate. Two or three series of experiments were made.

The tests were made as follows:

The M4Be human cell line (Jacubovich et al. Cancer Immunol. Immunother. 1979, 7, 59-64), a melanocytes cell line capable of producing melanines, was used in this study to determine the values of $CI_{50}$.

The cells were maintained in the Dulbecco modified Eagle medium with 10% of foetal calf serum (FCS), 1 mM of glutamine, 100 U/ml of penicillin and $10^{-4}$ g/ml of streptomycine.

All cell lines were maintained at 37° C. in an atmosphere with 5% of $CO_2$ and cell culture media were renewed every two days. The cells were applied in contact with a plate with 96 wells (Nunc, Roskilde) 24 hours before contact of dipeptides according to the invention.

AMPc was measured as follows:

Cells applied in contact the day before with $8\times10^4$ cells per well were put in the presence of one of the five dipeptide conjugates according to the invention at various concentrations for 10 minutes at 37° C. with $5\times10^{-8}$ M of α-MSH. After this time, the lysis of the cells was made and the AMPc content was measured using a connection test box by competition (RPN225, Amersham Pharmacia Biotech). Each independent experiment was carried out at least twice in triplicate.

The peptidic activity was determined with reference to the AMPc content synthesized by untreated cells and the production of AMPc induced by α-MSH alone. The curves were adjusted and the values of CI$_{50}$ were determined with non-linear regression in the GraphPad Prism (GraphPad software, San Diego, Calif., United States).

Table 2 below contains the results.

TABLE 2

Experiments on inhibition of AMPc production on M4Be cells

| Compound | Sequence | Purity (%) | CI50 (μM) exp1 | CI50 (μM) exp2 | CI50 (μM) exp3 | CI50 (μM) aver. |
|---|---|---|---|---|---|---|
| 39 | Palm-Arg-His-NH$_2$ | 94 | 29 | 4.6 | 4.4 | 13 |
| 41 | Palm-Arg-Arg-NH$_2$ | 100 | 36 | 17 | — | 26 |
| 49 | Palm-Arg-Pro-NH$_2$ | 87 | 20 | 26 | — | 23 |
| 50 | Palm-Arg-Lys-NH$_2$ | 100 | 48 | 9.6 | — | 29 |
| 125 | Palm-Ser-Pro-NH$_2$ | 100 | 45 | 5.5 | 1.0 | 17 |

Thus, unexpectedly, the tested Palm-dipeptides appeared to be antagonists of the human MC$_1$ receptor of melanocortine using M4Be melanoma cell lines. These dipeptide conjugates have a CI$_{50}$ within a micromolar range. These dipeptides are the first example of short synthesis antagonist compounds binding to the MC$_1$ receptor and they open up the field for small molecule non-peptidic antagonists of α-MSH.

In particular, these compounds comprise an arginine residue in position AA2. Interestingly, compound 125 (Palm-Ser-Pro-NH$_2$) does not have any basic residue in its sequence, and has a value of CI$_{50}$ equal to 17 μM. This result showed that the bond to the MC$_1$ receptor does not necessarily require a positively charged radical.

With only two amino acid residues, these palmitoyled compounds can be considered as being leader compounds useful for design of non-peptide antagonists of α-MSH.

The invention claimed is:

1. Dipeptide conjugate with general formula I below:

A-AA2-AA1-NH$_2$          I in which
A represents the radical corresponding to palmitic acid,
AA1 and AA2 represent identical or different amino acids selected from the group consisting of Pro, Arg, His, Lys, the corresponding homo-amino acids, and the corresponding beta-amino acids,
in the form of enantiomers or diastereoisomers and mixtures thereof including racemic mixtures,
with the proviso that at least one of the amino acids AA2 or AA1 is Arg and with the exception of the dipeptide conjugates Palm-Orn-Arg-NH$_2$ and Palm-Arg-Arg-NH$_2$.

2. Dipeptide conjugate according to claim 1, wherein AA2 represents a basic amino acid.

3. Dipeptide conjugate according to claim 1 wherein it is selected from among the group consisting of:
a) A-Arg-His-NH$_2$,
b) A-Arg-Pro-NH$_2$, and
c) A-Arg-Lys-NH$_2$,
in which the definition of A is as given in claim 1.

4. Dipeptide conjugate according to claim 1, wherein it is selected from among the group consisting of
39) Palm-Arg-His-NH$_2$,
49) Palm-Arg-Pro-NH$_2$, and
50) Palm-Arg-Lys-NH$_2$.

5. Cosmetic or pharmaceutical composition comprising a dipeptide conjugate according to claim 1, and possibly a cosmetically or pharmaceutically acceptable excipient.

6. Method for lightening or whitening the epidermis, for eliminating skin spots, or for preventing pigmentation of the epidermis comprising the administration of an effective amount of a cosmetic composition according to claim 5 or a cosmetic composition comprising the dipeptide Palm-Arg-Arg-NH$_2$ to a patient in need thereof.

7. Method according to claim 6, wherein the cosmetic composition is applied onto the skin.

8. Dipeptide conjugate according to claim 2, wherein AA2 is Arg.

9. Dipeptide conjugate according to claim 6, wherein the skin spots are age spots or freckles.

* * * * *